United States Patent [19]

Frey et al.

[11] Patent Number: 4,776,328
[45] Date of Patent: Oct. 11, 1988

[54] BONE NAIL AND AN INSTRUMENT FOR IMPLANTING A BONE NAIL

[75] Inventors: Otto Frey, Winterthur; Rudolf Koch, Berlingen, both of Fed. Rep. of Germany

[73] Assignee: Sulzer Brothers Limited, Winterthur, Switzerland

[21] Appl. No.: 35,991

[22] Filed: Apr. 8, 1987

[30] Foreign Application Priority Data

Apr. 15, 1986 [CH] Switzerland .................... 1491/86

[51] Int. Cl.⁴ .............................................. A61F 5/04
[52] U.S. Cl. .............................. 128/92 VT; 128/92 Y
[58] Field of Search ........ 128/92 YF, 92 VT, 92 YE, 128/92 YC, 92 Y; 411/481, 508–510, 923

[56] References Cited

U.S. PATENT DOCUMENTS

| 2,182 | 7/1841 | Ballard | 411/923 |
|---|---|---|---|
| 230,585 | 7/1880 | Soule | 411/923 |
| 257,351 | 5/1882 | Lubin | 411/481 |
| 373,291 | 11/1887 | Higgs | 411/481 |
| 405,972 | 6/1889 | Taylor | 411/481 |
| 797,494 | 8/1905 | Chase | 411/481 |
| 2,172,553 | 9/1939 | Tripp | 411/923 |
| 4,402,641 | 9/1983 | Arff | 411/510 |
| 4,423,721 | 1/1984 | Otte et al. | 128/92 VT |
| 4,462,395 | 7/1984 | Johnson | 128/92 VT |

FOREIGN PATENT DOCUMENTS

| 908558 | 4/1946 | France | 128/92 VT |
|---|---|---|---|
| 427703 | 2/1975 | U.S.S.R. | 128/92 VT |

Primary Examiner—Stephen C. Pellegrino
Assistant Examiner—Ralph Lewis
Attorney, Agent, or Firm—Kenyon & Kenyon

[57] ABSTRACT

The bone nail is provided with a tapered portion having a barbed denticulation and a conical head which has a conical shaped depression at the proximal end for receiving a centering cone of the setting and driving instrument. The instrument carries a movable sleeve at the distal end for engaging and holding the bone nail in alignment with the centering cone during implantation. The sleeve is movable relative to the distal end of the instrument so as to disengage from the conical head of the bone nail to permit removal of the instrument and subsequent replenishment of the instrument with a fresh bone nail. The sleeve includes an expandable distal section for engaging the conical head of the bone nail and a proximal expandable section for engaging about a conical surface of the instrument.

10 Claims, 2 Drawing Sheets

BONE NAIL AND AN INSTRUMENT FOR IMPLANTING A BONE NAIL

This invention relates to a bone nail and to an instrument for implanting a bone nail.

As is known, various types of bone nails have been used for fixing implants, for example, artificial partial surfaces of joints as described in Swiss Pat. No. 632,922 and of osteosynthetic plates in conjunction with clasps of artificial ligaments and tendons. In order to optimize the use of such bone nails, the nails are usually driven into a bone at an oblique angle. In this process, the direction of the orignnal "placing" of the nail on the bone must be kept as precisely as possible during driving in of the nail. Moreover, the demand for good and relatively easy removal must exist in order to be able to remove the nail, for example, when used with a temporary implant such as an osteosynthetic plate.

Accordingly, it is an object of the invention to provide a bone nail of optimum construction for both placement and removal purposes.

It is another object of the invention to provide an instrument for easily implanting a bone nail in place.

It is another object of the invention to be able to implant a bone nail in place in a reliable and efficient manner.

Briefly, the invention provides a bone nail which is comprised of a cylindrical stem, a tapered portion extending from the stem to a distal end and having a barbed denticulation thereon and a conical head extending from the stem to a proximal end and having a conical shaped depression at the proximal end. In addition, the conical head is provided with an annular surface about the depression which is disposed upon a conical angle relative to a longitudinal axis of the stem.

The denticulation includes a fine denticulation for engaging cortical tissue and a coarse denticulation for engaging spongiosa for anchoring purposes.

The invention also provides a setting and driving instrument which includes a cylindrical ram, a peg which extends coaxially from the ram and has a plurality of longitudinally spaced apart steps and a centering cone extending from the peg to a distal end. The cylindrical ram extends to a proximal end which is shaped for gripping by a surgeon as well as to serve as an anvil for hammering.

In addition, the instrument cooperates with a movable sleeve which is mounted on the distal end for engaging and holding a bone nail on the instrument. This sleeve includes a central section which is slidably mounted on the peg and a first expandable section extending from the central section to a proximal end. This expandable section has an inwardly directed projection engaging one of the steps on the peg at the proximal end so as to be retained on the instrument. The sleeve also has a second expandable section extending from tee central section to a distal end. This latter expandable section has an inwardly directed projection at the distal end opposite the centering cone of the instrument for engaging a conical head of a bone nail therebetween.

In conjunction with the centering cone of the instrument the conical shaped depression of a bone nail ensures a rigid coaxial connection of the bone nail to the instrument. Further, the sleeve encompasses the nail about the conical head practically along the entire circumference of the head and thus prevents migration of the nail from a coaxial position with the instrument during driving.

The sleeve also provides for independent separation of an implanted bone nail from the instrument at the end of a setting and driving operation. To this end, the expandable section at the distal end of the sleeve has an abutment surface with rounded edges to facilitate expansion of the distal section after implantation of a bone nail. During this expansion, the instrument drives the bone nail further into a bone while at the same time causing expansion of the distal end of the sleeve and longitudinal movement of the sleeve on the instrument. This, in turn, causes separation of the sleeve from the conical head of the bone nail. Once the nail has been detached, the instrument can be removed. At this time, the expandable nature of the distal end of the sleeve causes the distal end to reset about the centering cone of the instrument.

Advantageously, the peg of the instrument is provided with a first cylindrical surface for slidably receiving the central section of the sleeve, a second cylindrical surface proximally of this first cylindrical surface which is of a greater diameter than the first cylindrical surface, and a step between the two cylindrical surfaces for abutting the central section of the sleeve. The step thus acts as a stop for the sleeve during the driving process and prevents over expanding of the proximal expandable section of the sleeve on the instrument.

The expansion of the distal end of the sleeve during setting of nail is enhanced by the annular surface of the conical head of a bone nail. In addition, because of the conical shape of the nail head, a suitable removable instrument, for example, pliers, may be inserted under the head for extraction of the nail. This makes extraction of the nail from a bone considerably easy and simple.

These and other objects and advantages of the invention will become more apparent from the following detailed description taken in conjunction with the accompanying drawings wherein.

Figure 1:
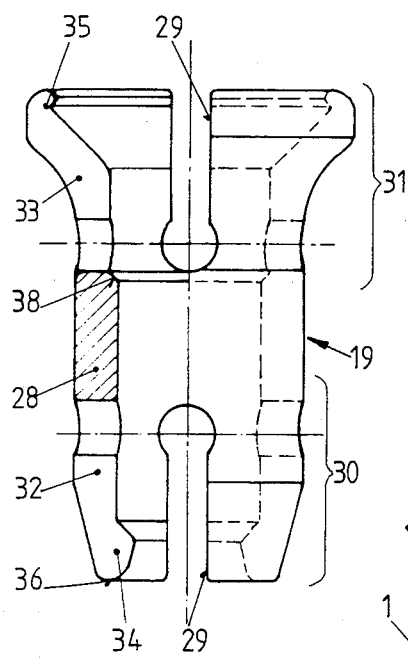
FIG. 1 illustrates a partial sectional view of a bone nail in accordance with the invention.

Referring to FIG. 1, the bone nail 1 has a cylindrical stem 3, a tapered portion 4 which extends from the stem 3 to a distal end and a conical head 2 extending from the stem 3 to a proximal end. The tapered portion 4 also includes a relatively fine denticulation 5 for penetrating cortical tissue when driven into a bone and a coarse denticulation 6 for anchoring the nail 1 in spongiosa. The fine denticulation 5 includes annular barb-like teeth which hook into the cortical tissue so that migration out of the tissue counter to a driving direction is securely prevented.

The conical head 2 is connected to the stem 3 via a constriction 9 and includes a conical shaped depression 11 at the proximal end which is coaxial of a longitudinal axis 10 of the nail 1. The conical head 2 also has an annular surface 12 about the depression 11 which is disposed on a conical angle relative to the longitudinal axis 10. As indicated, the annular surface 12 is slanted towards the outside for purposes as described below.

Figure 2:
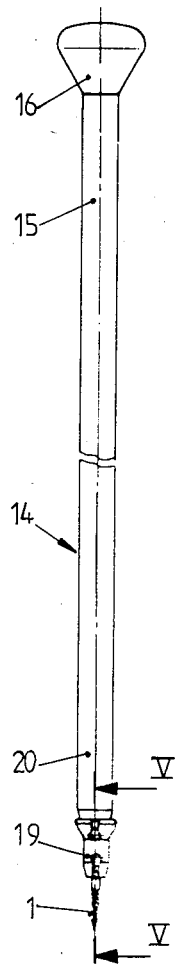
FIG. 2 illustrates a view of a setting and driving instrument and sleeve combination with a bone nail in place in accordance with the invention.

Referring to FIG. 2, a setting and driving instrument 14 is provided for driving a bone nail 1 into a bone (not shown). This instrument 14 includes a cylindrical ram 15 which carries a knob-like head 16 at the proximal end which serves, on the one hand, as a handle for a surgeon to guide the instrument during driving and, on the other hand, as an anvil against which a hammering tool may impact.

Figure 3:
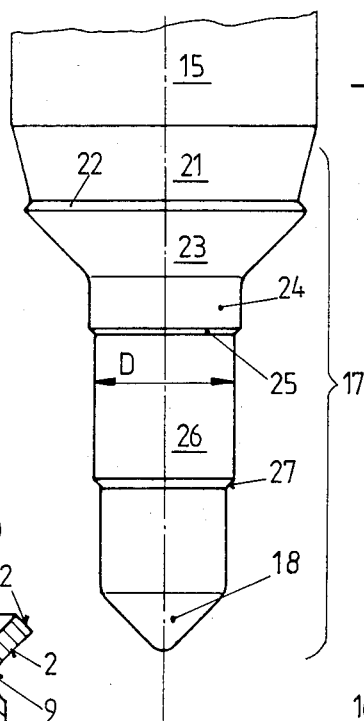
FIG. 3 illustrates an enlarged view of a distal end of the setting and driving instrument in accordance with the invention.

Referring to FIG. 3, the instrument 14 has a peg 17 extending coaxially from the ram 15 at the distal end. This peg 17 includes a centering cone 18 at the distal end as well as several contoured sections which are seperated by a plurality of longitudinally spaced apart steps. As indicated, a pair of conical sections 21, 23 which are separated by a conically shaped step 22 extend from the ram 16 to a cylindrical section 24. A second cylindrical section 26 which is of a reduced diameter D extends from a step 25 separating the cylindrical sections 24, 26 to a further step 27 which leads to a cylindrical section on which the centering cone 18 is formed.

The centering cone 18 of the instrument 14 forms a positive counterpart to the depression 11 at the proximal end of the nail 1.

Referring to FIG. 2, a movable sleeve 19 is mounted on the distal end of the instrument 14 for engaging and holding a bone nail 1 thereon so that the nail axis 10 and instrument axis 20 are aligned.

Figure 4:
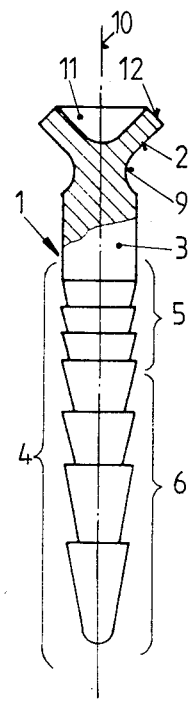
FIG. 4 illustrates a partial cross sectional view of a sleeve in accordance with the invention.
Figure 5:
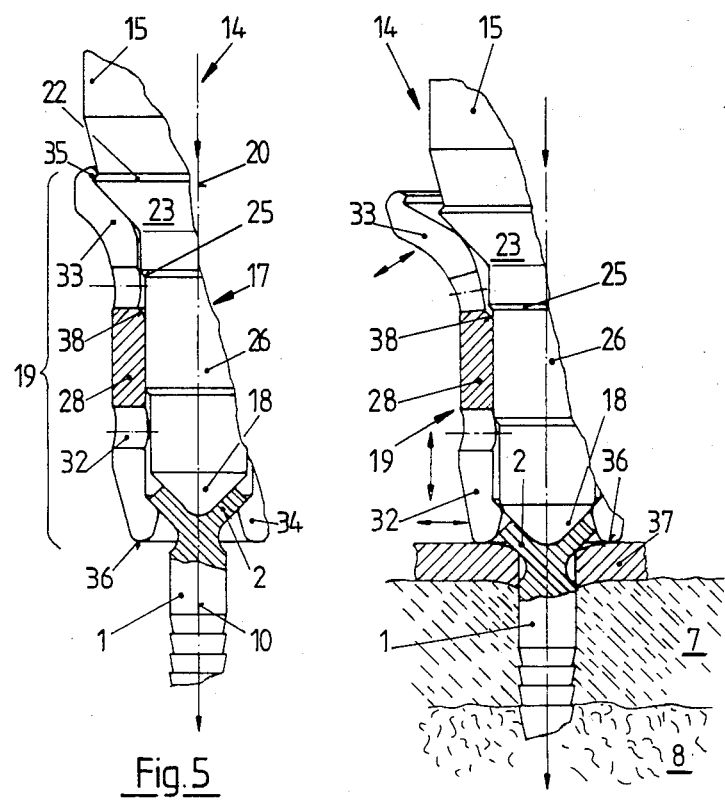
FIG. 5 illustrates a view taken on line V—V of FIG. 2.
Figure 6:
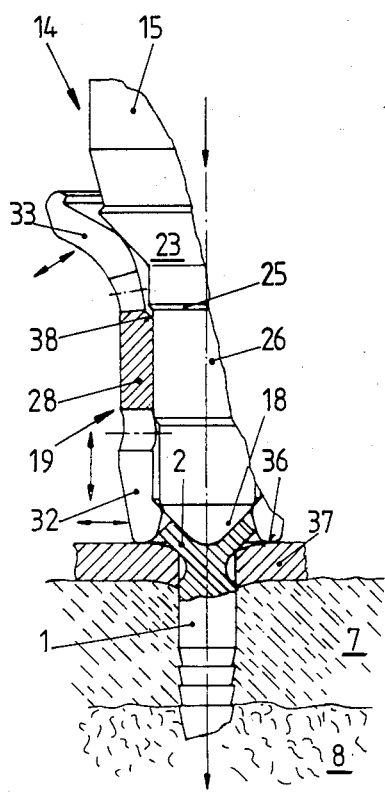
FIG. 6 illustrates the position of the setting and driving instrument and sleeve after implanting of a bone nail.

Referring to FIG. 4, the sleeve 19 has a central section 28 which is slidably mounted on the cylindrical surface 26 of the peg 17 and, to this end, has an inner diameter for sliding on the surface 26 in a slide-fit manner, for example as indicated in FIGS. 5 and 6. The sleeve 19 also has expandable sections 30, 31 extending from the central section 28 to the distal and proximal ends, respectively. As indicated, each expandable section 30, 31 is divided by slits 29 into four expandable flaps 32, 33, respectively, which terminate in nose-like projections 34, 35. The flaps 33 at the proximal end expand outwardly to form a hollow cone and carry a radially inwardly directed projection 35 at the proximal end for engaging over the conical step 22 of the peg 17 (see FIG. 5). The flaps 32 at the distal end each carry an inwardly directed projection at the distal end for disposition opposite the centering cone 18 of the peg 17 so as to engage the conical head 2 of a bone nail therebetween (see FIG. 5).

The sleeve 19 also includes an annular step 38 at the proximal end of the central section 28 for enlarging the inner diameter of the central section at the proximal end.

The flaps 32 are rounded at the distal end to form an abutting surface 36 for purposes as described below.

Referring to FIG. 5, when a bone nail 1 is engaged on the instrument 14 via the sleeve 19, the distal expandable section 30 of the sleeve 19 holds the bone nail 1 in a centered position on the cone 18 of the peg 17, i.e. in alignment with the axis 20 of the instrument 14. At the same time, the central section 28 is disposed about the cylindrical surface 26 of the peg 17 with the annular step 38 in spaced relation to the annular step 25 on the peg 17. Also, the flaps 33 are engaged against the conical surface 23 of the peg 17 with the projections 35 engaged around the conical step 22. The nail 1 is thus firmly held in place.

Figure 8:
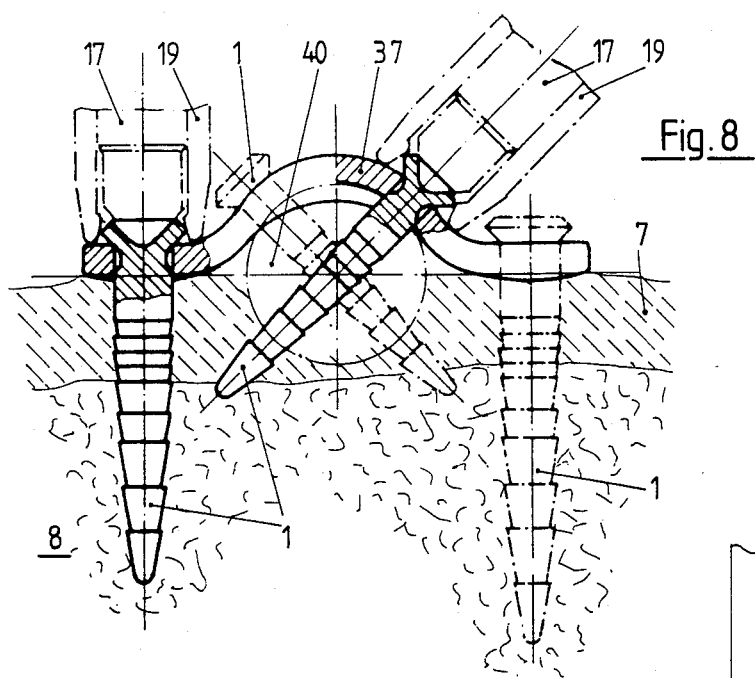
FIG. 8 illustrates a part cross sectional view of an anchorage of an artificial ligament to a bone utilizing bone nails according to the invention.

Referring to FIG. 6, when the nail 1 is driven into a bone, the nail usually passes through an implant 37, for example a clamp like clasp as indicated in FIG. 8. Alternatively, the nail may be driven directly into a bone.

After the nail 1 has been driven into the bone so that the coarse denticulation is in the spongiosa 8 and the fine denticulation is in the cortical tissue 7, the conical head 2 abuts against the implant 37. At this time, the rounded surfaces 36 at the distal end of the sleeve 19 engage the implant 37. Continued hammering of the instrument 14 causes further penetration of the bone nail so as to bring the conical head 2 into abutment with the implant 37. At the same time, the flaps 32 at the distal end of the sleeve 19 expand outwardly as indicated in by the double headed arrow while the central section 28 slides upwardly, as viewed, on the cylindrical surface 26 of the peg 17 as indicated by the double headed arrow. At the same time, the flaps 33 at the proximal end of the sleeve 19 expand outwardly as indicated by the double headed arrow. Relative movement of the peg 17 through the sleeve 19 is limited by the annular step 38 and, thus, expansion of the proximal end of the sleeve 19 is limited. At this time, the instrument may be removed along with the sleeve 19. Because of the elasticity of the sleeve, the flaps 32 re-engage with the cone 18 of the peg 17 and, together with the contraction of the flaps 33 at the proximal end on the conical surface 23, cause resetting of the sleeve 19 on the instrument 14 for re-engagement with a further nail.

Referring to FIG. 8, wherein like reference characters indicate like parts as above, in order to drive a nail 1 into the bone 7, 8, the following procedure is recommended for example.

First, after a nail 1 has been mounted on the instrument 14 as to form a firm unit, the unit is placed into the desired driving driving connection against the bone. Thereafter, an impacting tool (not shown) for example a hammer can be used to drive the nail into the bone. As soon as the abutment surfaces 36 of the sleeve 19 rest against the implant 37, the sleeve 19 is displaced by further blows relative to and on the peg 17 in an upward direction, as viewed. The flaps 33 then become expanded by the conical surface 23 so that the projections 35 separate from the step 22. Upon displacement of the sleeve 19, expansion of the flaps 32 occurs and the "locking" of the nail head 2 is cancelled.

On lifting the instrument 14, the elastic prestress in the flaps 33 cause an automatic resetting of the sleeve 19 into the "starting position". In this position, the projections 35 lock against the step 22 and the instrument 14 is ready to accept a new nail 1.

Figure 7:
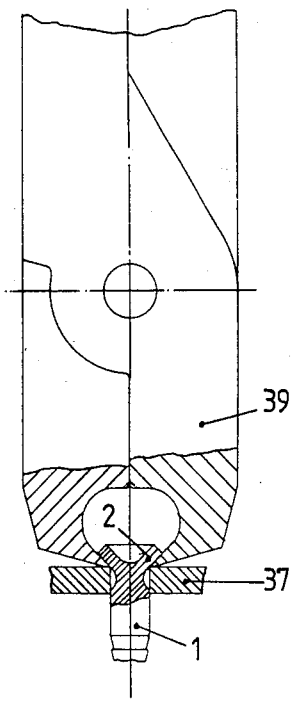
FIG. 7 illustrates a part sectional view of a pliers about a bone nail during removal of the bone nail.

Referring to FIG. 7, the conical form of the nail head 2 facilitates the action of a removal instrument, for example, pliers 39 in the event that a nail which had been inserted in connection with a temporary implant has to be removed from the bone.

As indicated in FIG. 8, several nails 1 may be used to anchor an artificial ligament 40 on a bone 7, 8 with the aid of a clasp 37. In this process, the nails may have different lengths depending on the structure of the bone. As indicated, two nails of differing length are driven approximately perpendicular to the bone surface in order to hold the clasp 37. Two additional nails are driven in obliquely through the ligament 40 into the bone 7, 8 in order to improve attachment of the ligament 40.

The materials used for the nail 1 are metals, preferably titanium or titanium alloys. However, other implant materials may also be used in the production of the nail. The setting and driving instrument 14 is made of materials customarily used for surgical instruments, for example "instrument" steel.

The invention thus provides a bone nail which can be readily implanted into a bone for anchoring purposes.

Further, the invention provides a driving and setting instrument and cooperating sleeve for accurately implanting a bone nail while at the same time providing for a quick and easy detachment of the instrument from the nail.

The invention also provides a setting and driving instrument which can be readily replenished with fresh bone nails for subsequent implanting operations.

What is claimed is:

1. In combination
   a setting and driving instrument including a cylindrical ram, a peg extending coaxially from said ram and having a plurality of longitudinally spaced apart steps and a centering cone extending from said peg to a distal end; and
   a movable sleeve including a central section slidably mounted on said peg, a first expandable section extending from said central section to a proximal end and having an inwardly directed projection engaging one of said steps of said peg at said proximal end and a second expandable section extending from said central section to a distal end and having an inwardly directed projection at said distal end opposite said centering cone of said instrument for engaging a conical head of a bone nail therebetween.

2. The combination as set forth in claim 1 wherein said second expandable section has an abutment surface at said distal end with rounded edges.

3. The combination as set forth in claim 1 wherein said peg includes a first cylindrical surface slidably receiving said central section of said sleeve, a second cylindrical surface proximally of said first cylindrical surface and of greater diameter than said first cylindrical surface and a step between said cylindrical surfaces for abutting said central section of said sleeve.

4. The combination as set forth in claim 1 wherein said step of said instrument is of greater diameter than an inner diameter of said projection of said proximal expandable section of said sleeve.

5. The combination as set forth in claim 1 wherein each expandable section of said sleeve is split.

6. The combination as set forth in claim 1 which further comprises a bone nail having a conical head engaged between said projection of said sleeve at said distal end and said cone of said instrument.

7. The combination as set forth in claim 6 wherein said head of said nail has a conical shaped depression receiving said cone of said instrument.

8. The combination as set forth in claim 1 which further comprises a bone nail having a cylindrical stem; a tapered portion extending from said stem to a distal end and having a barbed denticulation thereon; and a conical head extending from said stem to a proximal end and having a conical shaped depression at said proximal end.

9. The combination as set forth in claim 8 wherein said conical head has an annular surface about said depression, said annular surface being disposed on a conical angle relative to a longitudinal axis of said stem.

10. The combination as set forth in claim 8 wherein said denticulation includes a fine denticulation for engaging cortical tissue and a coarse denticulation for engaging spongiosa.

* * * * *

UNITED STATES PATENT AND TRADEMARK OFFICE
CERTIFICATE OF CORRECTION

PATENT NO. : 4,776,328

DATED : October 11, 1988

INVENTOR(S) : Otto Frey, et al

It is certified that error appears in the above-identified patent and that said Letters Patent is hereby corrected as shown below:

```
Column 1, line 14 "orignnal" should be -original-
Column 1, line 58 "tee" should be -the-
Column 3, line 24 "seperated" should be -separated-
Column 4, line 44 "driving driving" should be -driving-
Column 5, line 7  "preferra-" should be --prefera- --
```

Signed and Sealed this

Fourteenth Day of March, 1989

Attest:

DONALD J. QUIGG

*Attesting Officer*     *Commissioner of Patents and Trademarks*